US00PP37614P2

(12) United States Plant Patent
Suiker

(10) Patent No.: US PP37,614 P2
(45) Date of Patent: Aug. 18, 2026

(54) STRAWBERRY PLANT NAMED 'Ferris'

(50) Latin Name: ***Fragaria* x *ananassa***
Varietal Denomination: Ferris

(71) Applicant: Flevo Berry Holding B.V., Ens (NL)

(72) Inventor: Marcel Suiker, Ens (NL)

(73) Assignee: Flevo Berry Holding B.V., Ens (NL)

( * ) Notice: Subject to any disclaimer, the term of this patent is extended or adjusted under 35 U.S.C. 154(b) by 0 days.

(21) Appl. No.: 19/462,883

(22) Filed: Jan. 28, 2026

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
See application file for complete search history.

(56) References Cited

U.S. PATENT DOCUMENTS

PP34,684 P2 * 10/2022 Suiker ..... Plt./208

* cited by examiner

*Primary Examiner* — Susan Mccormick Ewoldt
*Assistant Examiner* — Zachariah Allan Kay
(74) *Attorney, Agent, or Firm* — James R. Holm; Plant Novelty Rights, LLC

(57) ABSTRACT

A new and distinct strawberry plant named 'Ferris' particularly distinguished by a semi-upright growth habit with medium foliage density, orange-red colored fruit with a soft texture and slightly sweet and moderately acidic flavor, conical shaped fruit with a smooth and glossy appearance, and absent to very limited stolon formation.

4 Drawing Sheets

Figure 1:
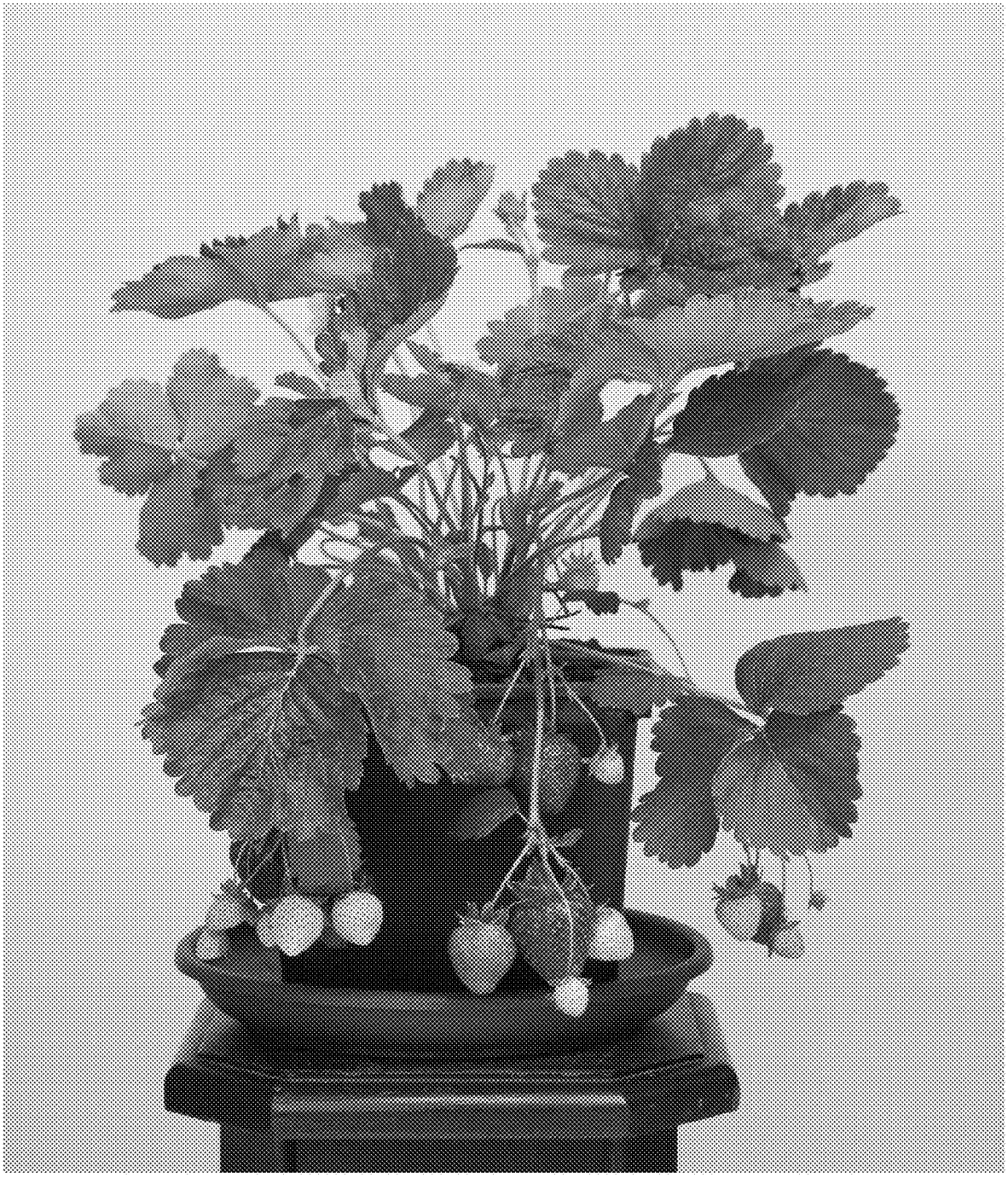

Genus and species: *Fragaria* x *ananassa*.
Variety denomination: 'Ferris'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date. Plant Breeder's Rights for this variety have been applied for under CPVO application No. 2024/2220 on Sep. 23, 2024.

BACKGROUND OF THE NEW PLANT

The present invention comprises a new and distinct variety of strawberry plant, botanically known as *Fragaria* x *ananassa*, and hereinafter referred to by the variety name 'Ferris'. The new strawberry variety 'Ferris' is a seedling selection that resulted from a controlled pollination breeding program carried out in April of 2011 in Ens, Netherlands. The new variety originated as a seedling from crossing the proprietary strawberry breeding line '06-095' (unpatented), as the seed parent, with the proprietary strawberry breeding line '07-071' (unpatented) as the pollen parent. Seed from said cross was harvested, then germinated, and the resulting seedlings were grown to a mature size in order to evaluate for desirable commercial characteristics. In August of 2012, the inventor selected the claimed strawberry variety from amongst said seedlings for further evaluation to determine its distinctness and stability of the unique characteristics first observed.

Asexual reproduction of 'Ferris', by way of vegetative cuttings, was first performed in September of 2012 in Ens, Netherlands. Through twelve subsequent generations of asexual propagation, the unique features of this new strawberry variety 'Ferris' have proven to be stable and remain true to type.

SUMMARY OF THE INVENTION

The new strawberry variety 'Ferris' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new strawberry variety. The combination of these characteristics distinguishes 'Ferris' as a new and distinct variety of strawberry.

1. Strawberry 'Ferris' exhibits a semi-upright growth habit with medium foliage density;
2. Strawberry 'Ferris' exhibits orange-red fruit with a soft texture and slightly sweet and moderately acidic flavor;
3. Strawberry 'Ferris' exhibits conical shaped fruit with a smooth and glossy appearance; and
4. Strawberry 'Ferris' exhibits absent to very limited stolon formation.

DESCRIPTION OF THE PHOTOGRAPHS

This new strawberry variety is illustrated by the accompanying-colored photographs which show the overall appearance and distinct characteristics of the plant. The colors shown are as true as can be reasonably obtained by conventional photographic procedures. The photographs are of 12-month-old plants grown in 19-centimeter square containers in a conventional cold-story glasshouse in Ens, Netherlands. Colors in the photographs may differ slightly from the color values cited in the botanical description which accurately describes the colors of the new variety.

FIG. 1. shows the overall plant form, foliage, and fruit of 'Ferris'.

Figure 2:
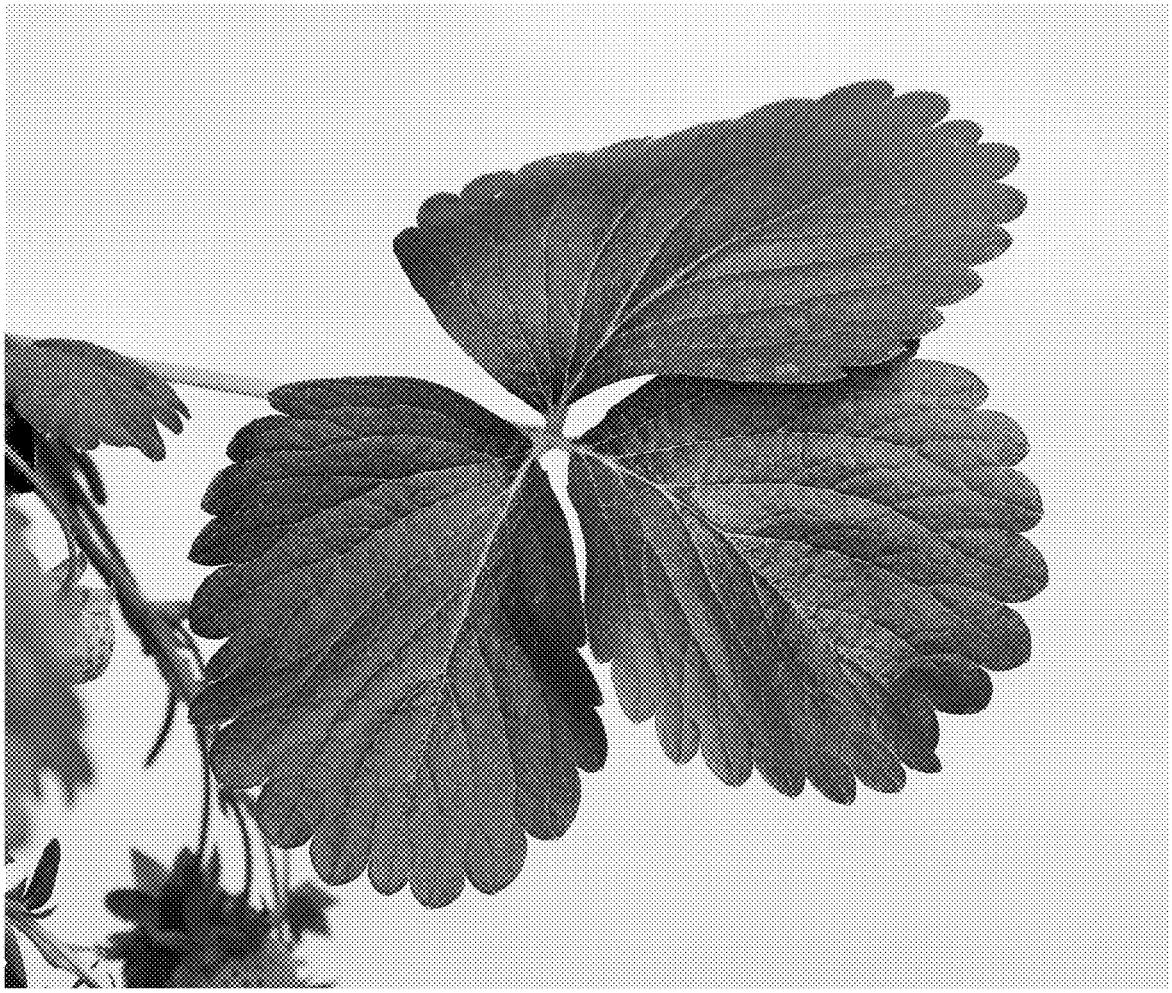

FIG. 2. shows a close-up of a typical leaf observed on plants of 'Ferris'.

Figure 3:
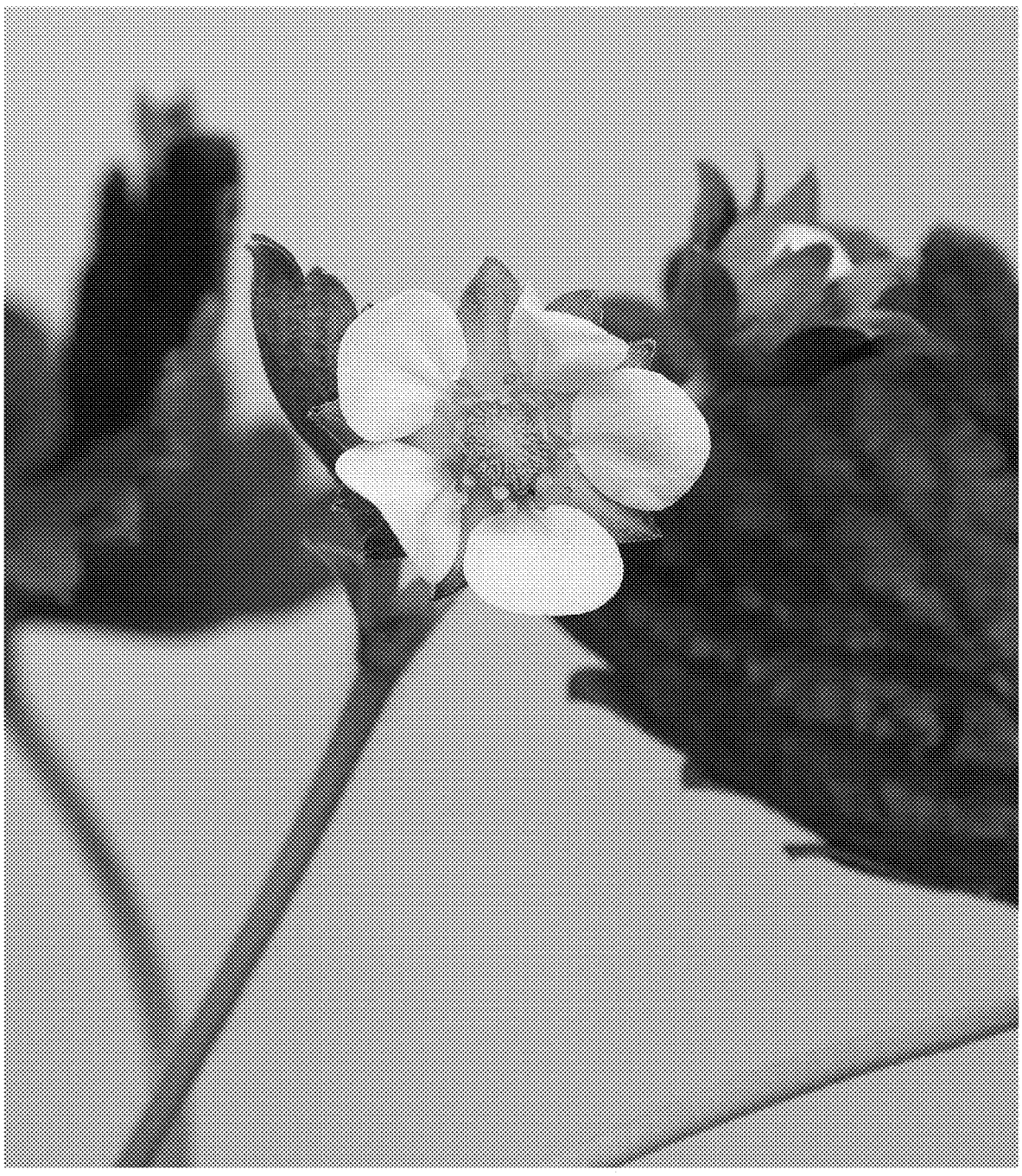

FIG. 3. shows a close-up of a typical flower observed on plants of 'Ferris'.

Figure 4:
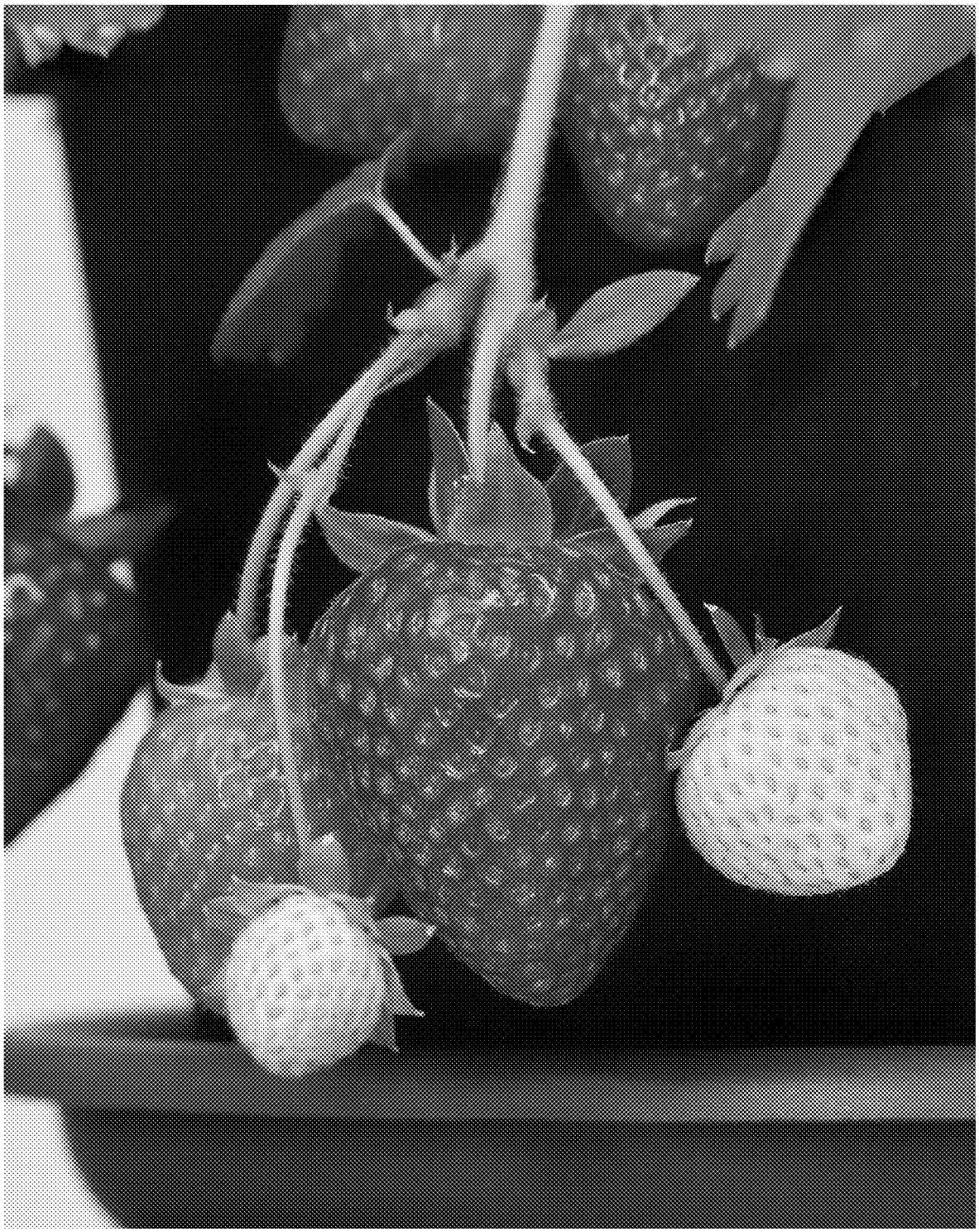

FIG. 4. shows typical fruit observed on plants of 'Ferris'.

DESCRIPTION OF THE NEW VARIETY

The following is a detailed botanical description of the new and distinct variety of strawberry known as 'Ferris', based upon observations of 12-month-old plants grown in 19-centimeter square containers in a conventional cold greenhouse located in Ens, Netherlands. Plants were grown on benches in a non-climate-controlled greenhouse, using conventional production protocols for strawberry plants which consisted of drip irrigation with fertigation applications as needed. Biological insect control measures were utilized in production. Plants were produced with full sun exposure and no photoperiodic treatments or artificial light was given to the plants. Temperatures ranged from 18 to 30 degrees Celsius during the day and 5 to 18 degrees Celsius at night. Observation data was recorded in September of 2025. Those skilled in the art will appreciate that certain characteristics will vary with older or, conversely, with younger plants. 'Ferris' has not been observed under all possible environmental conditions. Where dimensions, sizes, colors and other characteristics are given, it is to be understood that such characteristics are approximations or averages set forth as accurately as practicable. The phenotype of the new variety may differ from the descriptions set forth herein with variations in environmental, climatic and cultural conditions. In the following description, color references are made to The Royal Horticultural Society Colour Chart, Sixth Edition 2019 reprint, except where general color terms of ordinary dictionary significance are used.

DETAILED BOTANICAL DESCRIPTION

Classification:

*Family*.—Rosaceae.

*Botanical*.—*Fragaria* x *ananassa*.

*Denomination*.—'Ferris'.

*Common name*.—Strawberry.

Plant description:

*General*.—Acaulescent, herbaceous perennial with leaves and inflorescence developing from basal rosettes with approximately 5 rosettes per plant; no lateral branching and absent to very limited stolon formation.

*Growth habit*.—Semi-upright.

*Overall plant shape*.—Flattened.

*Average height*.—25.4 cm to the top of the foliar plane; 23.9 cm to the top of the floral plane.

*Average width*.—55.2 cm.

*Plant vigor*.—Moderate.

*Growth rate*.—Moderate.

Foliage description:

*Arrangement*.—Alternate.

*Attachment*.—Petiolate.

*Division*.—Trifoliate.

*Compound leaf outline*.—Broad reniform.

*Length*.—14.4 cm, excluding the petiole.

*Width*.—17.0 cm.

*Quantity*.—4 leaves per rosette.

*Leaflets*.—Quantity: 3.Shape: Varying from broad obovate to broad ovate, occasionally near orbicular. Length: 9.2 cm. Width: 8.9 cm. Aspect: Slightly concave. Apex: Minutely abruptly acute. Base: Broad attenuate to near obtuse. Margin: Coarsely dentate to crenate. Texture: Adaxial surface: Smooth except for the main vein and secondary veins which are very sparsely covered with very thin, soft hairs with an average length of 0.15 cm; hairs are colored a transparent white but too small and too sparsely present to measure R.H.S. color designation. Abaxial surface: Smooth except for the main vein and secondary veins which are moderately covered with very thin, soft adpressed hairs with an average length of 0.1 cm; hairs are colored a transparent 157D (green-white). Rugosity (adaxial and abaxial surfaces): Slightly rugose. Luster: Adaxial surface: Slightly glossy. Abaxial surface: Matte. Color: Juvenile foliage: Adaxial surface: Near 144A (yellow-green). Abaxial surface: Near 143C (green). Mature foliage: Adaxial surface: Near NN137A (green). Abaxial surface: Near 147B (yellow-green). Venation: Type: Pinnate. Color (mature leaf): Adaxial surface: Near N144C (yellow-green). Abaxial surface: Near 145B (yellow-green).

*Petiole*.—Length: 22.1 cm. Diameter: 0.3 cm, horizontal and vertical; petioles flattened on the adaxial surface. Strength: Strong. Texture: Moderately covered with very thin, soft hairs with an average length of 0.1 cm; hairs are colored a transparent white but too small and too sparsely present to measure R.H.S. color designation. Luster (adaxial and abaxial surfaces): Slightly glossy. Color (adaxial and abaxial surfaces): Near 144C (yellow-green).

*Stipules*.—General: Two leafy stipules present at the base of each leaf. Shape: Lanceolate. Length: 2.9 cm. Width: 0.6 cm. Apex: Narrow acute. Base: Broad cuneate. Color (adaxial and abaxial surfaces): Near 145A to 145B (yellow-green). Texture: Adaxial surface: Glabrous. Abaxial surface: Covered with very thin, soft hairs with an average length of 0.1 cm; hairs are colored a transparent white but too small and too sparsely present to measure R.H.S. color designation.

Inflorescence description:

*Type*.—Compound cymose panicle.

*Natural flowering season*.—From spring into summer in Ens, Netherlands.

*Time to flower*.—9 months.

*Length*.—4.8 cm, excluding the peduncle.

*Diameter*.—6.2 cm.

*Quantity of flowers per inflorescence*.—Approximately 5.

*Quantity of flower buds per plant*.—Approximately 28.

*Quantity of flowers per plant*.—Approximately 50.

*Quantity of flowers and flower buds per plant*.—Approximately 50.

*Peduncle*.—Length: 17.7 cm. Diameter: 0.3 cm. Aspect: Average of 70 degrees to horizontal. Strength: Moderate to strong. Texture: Densely covered with thin, soft hairs with an average length of 0.15 cm; hairs are colored a transparent near 156D (greyed-white) and lighter. Luster: Slightly glossy. Color: Near 144C (yellow-green).

Flower buds:

*Shape*.—Ovate.

*Length*.—1.2 cm.

*Diameter*.—1.2 cm.

*Texture*.—Smooth and glabrous except for the immature sepals which are moderately covered with thin, soft hairs with an average length of 0.75 mm; hairs are colored a transparent white but too small and too sparsely present to measure R.H.S. color designation.

*Luster*.—Matte.

*Color*.—Near 138B (green) and fading at the base to near 145B (yellow-green).

Flower:

*Form*.—Rotate; single.

*Aspect*.—Outwardly to upright.

*Habit*.—Low to moderate.

*Vertical height*.—3.3 cm.

*Horizontal diameter*.—3.3 cm.

*Depth*.—1.7 cm.

*Fragrance*.—Faintly sweet.

*Lastingness*.—Approximately 7 days.

*Persistence*.—Self-cleaning.

*Pedicels*.—Length: 2.3 cm. Diameter: 0.2 cm. Aspect: Approximately 30 degrees to the peduncle axis. Strength: Moderate. Texture: Densely covered with thin, soft hairs with an average length of 0.1 cm; hairs are colored a transparent near NN155D (white). Luster: Slightly glossy. Color: Near 144C (yellow-green).

*Petals*.—Arrangement: Rotate with a single whorl of free petals. Quantity: Average 6, varying between 5 and 8. Shape: Near orbicular and slightly concave. Length: 1.4 cm. Width: 1.5 cm. Apex: Obtuse. Base: Broad cuneate. Margin: Entire, moderately undulated. Texture (adaxial and abaxial surfaces): Glabrous, smooth and moderately velvety. Rugosity: Non-rugose. Luster (adaxial and abaxial surfaces): Matte. Color when opening: Adaxial surface: NN155D (white) and fading at the base to near NN155A (white). Abaxial surface: NN155D (white) and fading at the base to near NN155A (white). Color when fully opened: Adaxial surface: NN155C (white) and fading at the base to near NN155A (white). Abaxial surface: NN155D (white) and fading at the base to near NN155A (white). Color when fading (adaxial and abaxial surfaces): Petals do not fade with age. Venation color when fully opened (adaxial and abaxial surfaces): Not visible.

*Calyx*.—Shape: Rotate. Length: 0.8 cm. Diameter: 3.1 cm. Sepals: Arrangement: Rotate with sepals in a single whorl and fused at the base. Quantity: Average 12, varying between 10 and 15. Length: 1.4 cm. Width: 0.55 cm. Shape: Elliptic. Apex: Acute. Base: Cuneate. Margin: Entire, occasionally with a single tooth present on one side and sometimes both sides. Texture: Adaxial surface: Smooth, covered with very thin, soft hairs with an average length of 0.1 cm; hairs are colored a transparent white but too small and too sparsely present to measure R.H.S. color designation. Abaxial surface: Smooth, covered with very thin, soft hairs with an average length of 0.1 cm; hairs are colored a transparent green-white, close to 157D, but too small to accurately measure R.H.S. color designation. Luster (adaxial and abaxial surfaces): Matte. Color when opening: Adaxial surface: Near 143A (green). Abaxial surface: Near 137B (green). Color when fully opened: Adaxial surface: Slightly darker than a blend of 141A and 143A (green). Abaxial surface: Near 138B (green). Sepal spurs: Not present.

*Bracts*.—Position: Two bracts are present at the base of each pedicel. Shape: Narrow elliptic to slightly carinate. Length: 2.3 cm. Width: 1.3 cm. Apex: Acute. Base: Attenuate. Margins: Serrate to dentate-serrate. Color: Adaxial surface: 137A (green). Abaxial surface: A blend of near 138B (green) and 147B (yellow-green). Texture: Adaxial surface: Very sparsely covered with thin, soft hairs with an average length of 0.5 mm; hairs are colored a transparent white but too small and too sparsely present to measure R.H.S. color designation. Abaxial surface: Moderately covered with thin, soft hairs with an average length of 0.75 cm; hairs are colored a transparent white but too small and too sparsely present to measure R.H.S. color designation.

Reproductive organs:

*Stamens*.—Quantity per flower: Average 28, varying between 24 and 32. Anthers: Shape: Oblong. Length: 1.25 mm. Width: 0.75 mm. Color: 13B (yellow). Filaments: Length: 0.3 cm. Color: Near 145D (yellow-green). Pollen: Abundance: Low. Color: Near 13A to 13B (yellow).

*Pistil*.—Quantity per flower: 300. Length: 0.1 cm. Style: Length: 0.7 mm. Color: Near 151B (yellow-green). Stigma: Shape: Club-shaped. Length: 0.3 mm. Diameter: 0.3 mm. Color: Near 151D (yellow-green).

Ovary color: Near 145B (yellow-green).

Seed and fruit:

*Fruit*.—Harvest season: May through September in the Netherlands. Time to maturity: Approximately 5 weeks after flowering. Quantity per plant: 20. Dimensions: 3.4 cm long and 3.3 cm in diameter. Weight: Average 15.2 grams. Shape: Conical. Texture: Smooth and sparsely to moderately covered with very short, soft hairs with an average length of 0.4 mm; hairs are colored white but too small and too sparsely present to measure R.H.S. color designation. Luster: Glossy. Color (mature fruit): Near N34A (orange-red). Fruit flavor: Slightly sweet and moderately acidic. Firmness of flesh: Very soft. Lastingness of fruit: Approximately 1 week. Market use: Fresh fruit market.

*Achenes*.—Position: Below surface. Quantity per fruit: 200. Length: 0.125 cm. Diameter 0.08 cm. Texture: Smooth and glabrous. Color: Near 167B (greyed-orange).

Environmental tolerances: Adapted to USDA Zones 4 through 9 and temperatures ranging from at least minus 32 degrees Celsius to 40 degrees Celsius; low to moderate tolerance to rain; moderate to high tolerance to wind.

Disease and pest tolerance: No claims are made to any superior disease or insect resistance or tolerance.

COMPARISON WITH THE PARENT PLANTS

The new strawberry variety 'Ferris' can be distinguished from its seed parent '06-095' (unpatented) in the following characteristics described in Table 1 below.

TABLE 1

| Characteristic | 'Ferris' | '06-095' |
|---|---|---|
| Plant habit. | More compact and semi-upright. | More spreading and less compact. |
| Stolon formation. | Absent to very limited. | Abundant. |
| Fruit shape. | Uniformly conical. | Short conical to more rounded. |
| Mature fruit external color. | Orange-red. | Deeper red. |
| Fruit surface appearance. | Very smooth and glossy. | Less glossy surface. |

The new strawberry variety 'Ferris' can be distinguished from its pollen parent '07-071' (unpatented) in the following characteristics described in Table 2 below.

TABLE 2

| Characteristic | 'Ferris' | '07-071' |
|---|---|---|
| Plant habit. | More compact and semi-upright. | More spreading with elongated runners. |
| Stolon length and visibility. | Absent to very limited stolon formation. | Abundant, long and highly visible. |
| Leaf position. | Held more upright and clustered. | More widely spaced and spreading. |

TABLE 2-continued

| Characteristic | 'Ferris' | '07-071' |
|---|---|---|
| Fruit position. | Held closer to the foliage and container. | Fruit hangs lower on long peduncles. |
| Fruit shape. | Uniformly conical. | More variable, some short conical to rounded. |

COMPARISON WITH RELATED KNOWN VARIETY

The new strawberry variety 'Ferris' can be distinguished from the related known variety of strawberry plant 'Florice' (U.S. Plant Pat. No. 34,684) in the following characteristics described in Table 3 below.

TABLE 3

| Characteristic | 'Ferris' | 'Florice' |
|---|---|---|
| Plant profile. | Flattened. | Flattened globular. |
| Plant height to the top of the foliar plane. | Approximately 25.4 cm | Approximately 20.5 cm. |
| Stolon formation. | Absent to very limited. | Present. |
| Fruit shape. | Conical. | Short conical. |
| Mature fruit external color. | Orange-red. | Red. |
| Fruit flesh texture. | Very soft. | Firm. |
| Fruit flavor. | Slightly sweet and moderately acidic. | Sweet and slightly acidic. |

What is claimed is:

1. A new and distinct variety of strawberry plant named 'Ferris', substantially as illustrated and described herein.

* * * * *